US008906086B2

(12) United States Patent
Roeder et al.

(10) Patent No.: US 8,906,086 B2
(45) Date of Patent: Dec. 9, 2014

(54) ENDOVASCULAR STENT GRAFT WITH SELF-CLOSING PERFUSION BRANCH

(71) Applicant: Cook Medical Technologies LLC, Bloomington, IN (US)

(72) Inventors: Blayne Roeder, Lafayette, IN (US); David Hartley, Wannanup (AU)

(73) Assignee: Cook Medical Technologies LLC, Bloomington, IN (US)

( * ) Notice: Subject to any disclaimer, the term of this patent is extended or adjusted under 35 U.S.C. 154(b) by 110 days.

(21) Appl. No.: 13/843,075

(22) Filed: Mar. 15, 2013

(65) Prior Publication Data

US 2014/0277369 A1    Sep. 18, 2014

(51) Int. Cl.
*A61F 2/06* (2013.01)
*A61F 2/856* (2013.01)
*A61F 2/07* (2013.01)

(52) U.S. Cl.
CPC .. *A61F 2/856* (2013.01); *A61F 2/07* (2013.01)
USPC .......................... 623/1.35; 623/1.13; 623/1.16

(58) Field of Classification Search
CPC ................ A61F 2/07; A61F 2/82; A61F 2/91
USPC .............................. 623/1.13, 1.15, 1.16, 1.35
See application file for complete search history.

(56) References Cited

U.S. PATENT DOCUMENTS

| 8,167,926 B2 * | 5/2012 | Hartley et al. ............... 623/1.13 |
| 2008/0114446 A1 * | 5/2008 | Hartley et al. ............... 623/1.13 |

* cited by examiner

*Primary Examiner* — Jason-Dennis Stewart
(74) *Attorney, Agent, or Firm* — Brinks Gilson & Lione

(57) ABSTRACT

A prosthesis having a tubular body of a biocompatible graft material having a proximal end, a distal end, a lumen therethrough, and a sidewall. The prosthesis includes at least one perfusion branch extending from the sidewall of the tubular body and having a proximal end, a distal end, and a lumen therethrough, where the lumen of the perfusion branch is in temporary fluid communication with the lumen of the tubular body. The perfusion branch comprises a self-sealing component, that after predetermined period of time precludes fluid flow out of the distal end of the perfusion branch.

20 Claims, 5 Drawing Sheets

ENDOVASCULAR STENT GRAFT WITH SELF-CLOSING PERFUSION BRANCH

TECHNICAL FIELD

This invention relates to a medical device for use in relation to endovascular surgery.

BACKGROUND

Stent grafts, including fenestrated, branched and bifurcated stent grafts, for the treatment of aortic and thoracoabdominal aneurysms and other related vascular diseases are well known. One of the major complications associated with surgical treatment of thoracic and thoracoabdominal aortic aneurysms using a stent graft is paraplegia. During surgical repair, the intercostal and/or lumbar arteries may be acutely occluded resulting in a loss of blood circulation to the spinal arteries and ultimately leading to paraplegia.

Some current stent grafts include a perfusion branch that is similar to branches used to connect bridging stents to the renal arteries. The perfusion branch perfuses the aneurysm sac and allows blood circulation to the spinal arteries during surgery. These perfusion branches require a separate procedure after implantation to seal the perfusion branch from the aneurysm with a vascular occluder and prevent blood flow to the aneurysm. To overcome this limitation, it would be advantageous to provide a self-closing perfusion branch that does not require a separate surgery to seal the perfusion branch from the aneurysm.

BRIEF SUMMARY

A prosthesis having a tubular body of a biocompatible graft material having a proximal end, a distal end, a lumen therethrough, and a sidewall. The prosthesis includes at least one perfusion branch extending from the sidewall of the tubular body and having a proximal end, a distal end, and a lumen therethrough, where the lumen of the perfusion branch is in temporary fluid communication with the lumen of the tubular body. The perfusion branch comprises a self-sealing component, that after predetermined period of time precludes fluid flow out of the distal end of the perfusion branch.

In one embodiment, the self-sealing component comprises a flap element and a biodegradable attachment. The biodegradable attachment may comprise one or more dissolvable sutures, staples, clips, adhesive or the like.

The self-sealing component may include a biasing element. The biasing element may comprise bi-stable properties.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

DETAILED DESCRIPTION

As used here, the term "distal" furthest from the heart during a procedure and "proximal" means closest to the heart during a procedure. These terms will be understood with reference to the figures.

Figure 1:
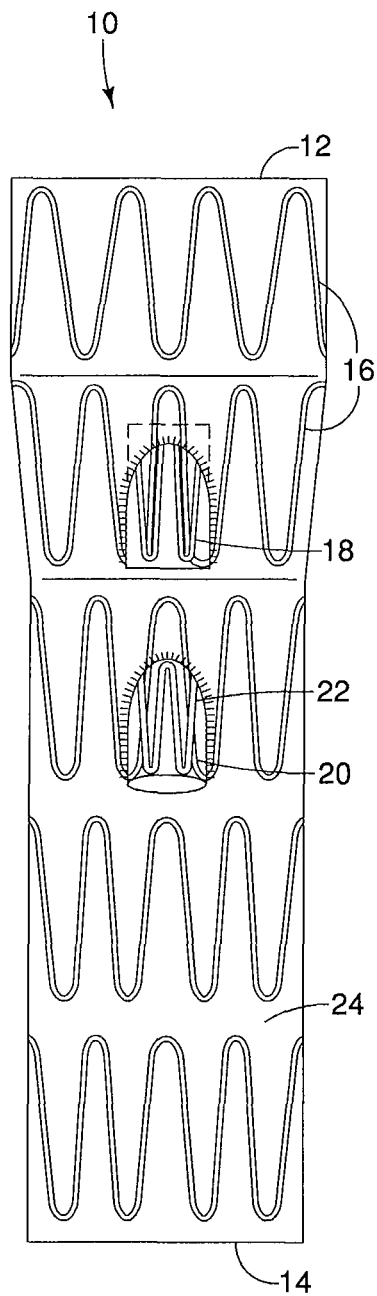
FIG. 1 is a front view of an example of a branch stent-graft.
Figure 2:
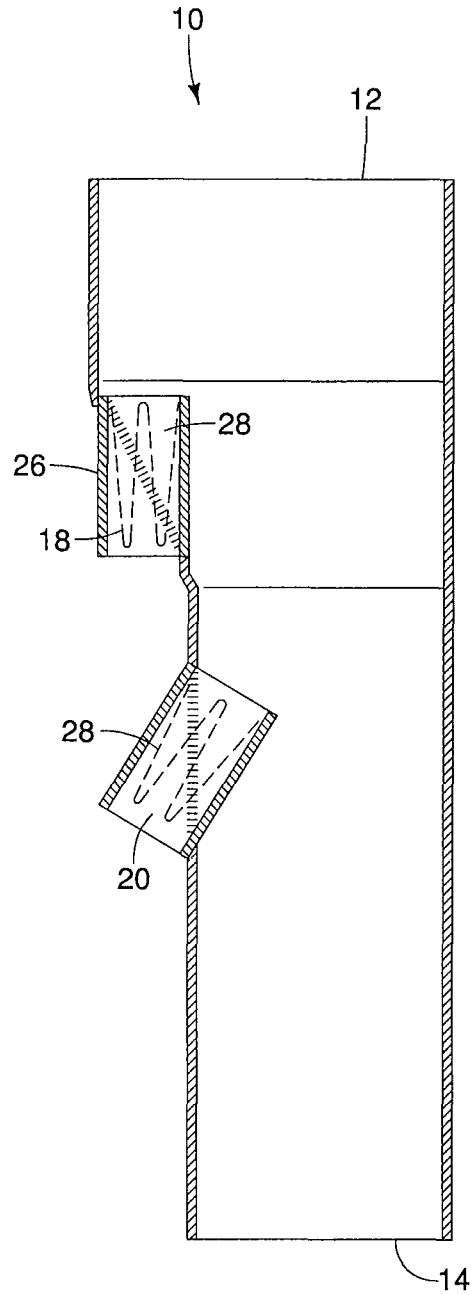
FIG. 2 is a side sectional view of FIG. 1.

FIG. 1 shows a stent-graft 10 having a proximal end 12 and a distal end 14 with one or more stents 16 attached to the graft 24. Stent-graft 10 has one or more branches 18, 20 at least partially extending from the external surface of the stent-graft 10. As shown in FIG. 2, the branches 18, 20 may have a portion 26 that extends from the outer surface of the stent-graft 10, and a portion 28 that extends into the lumen of the stent-graft 10. In other embodiments, the branch may extend entirely from the outer surface or entirely from the inner surface into the lumen. Branches may have one or more stents supporting them as shown in FIGS. 1 and 2. The stents may be external as shown at numeral 22 or internal as shown in FIG. 2 at numeral 28. One or more of the branches may be used to connect up with a branch vessel branching from the main body vessel into which stent-graft 10 has been placed. Further branch extensions may be inserted into the branches. Although the presently described embodiment shows only two branches, a device having three or more branches is also contemplated.

At least one of the branches may be provided as a perfusion branch. A perfusion branch is a branch that is temporarily left open to perfuse the sac of an aneurysm. Perfusion of the sac for a short time may encourage collateral blood vessels to form and reduce the chance of paraplegia. Perfusion branches have been used, but require a secondary procedure upon completion of the initial procedure to occlude them with a vascular occlude.

FIGS. 3-10 illustrate devices that are self-closing perfusion systems that do not require any additional procedure or component to close when it is desirable to close the perfusion branch.

Figure 3:
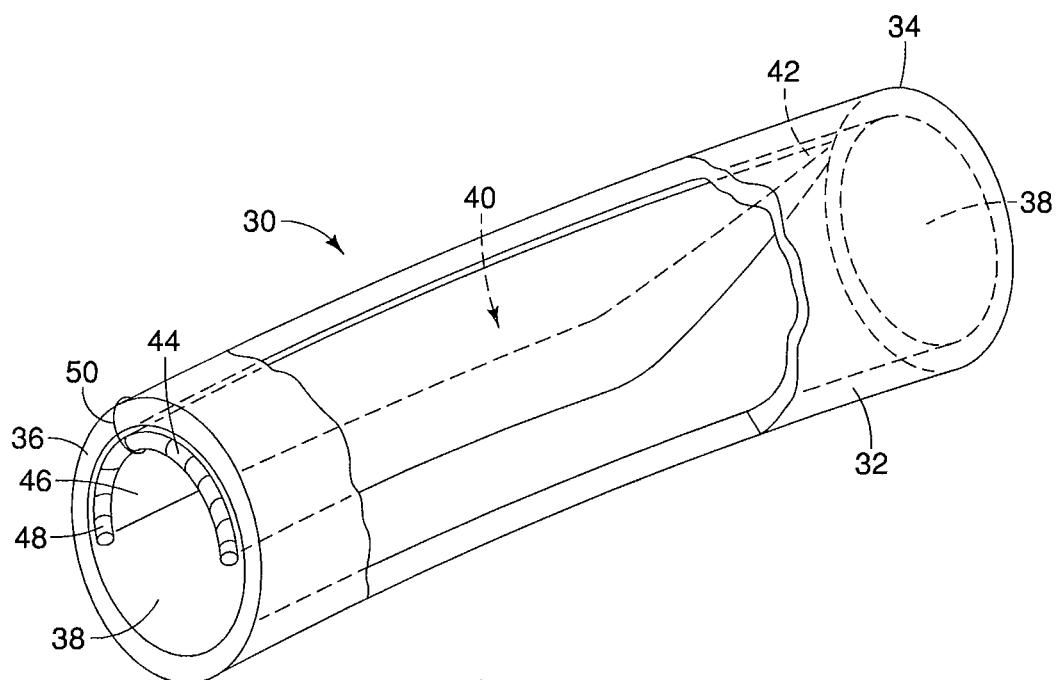
FIG. 3 is a perspective of a first embodiment of a perfusion branch of a stent graft in an open state.
Figure 4:
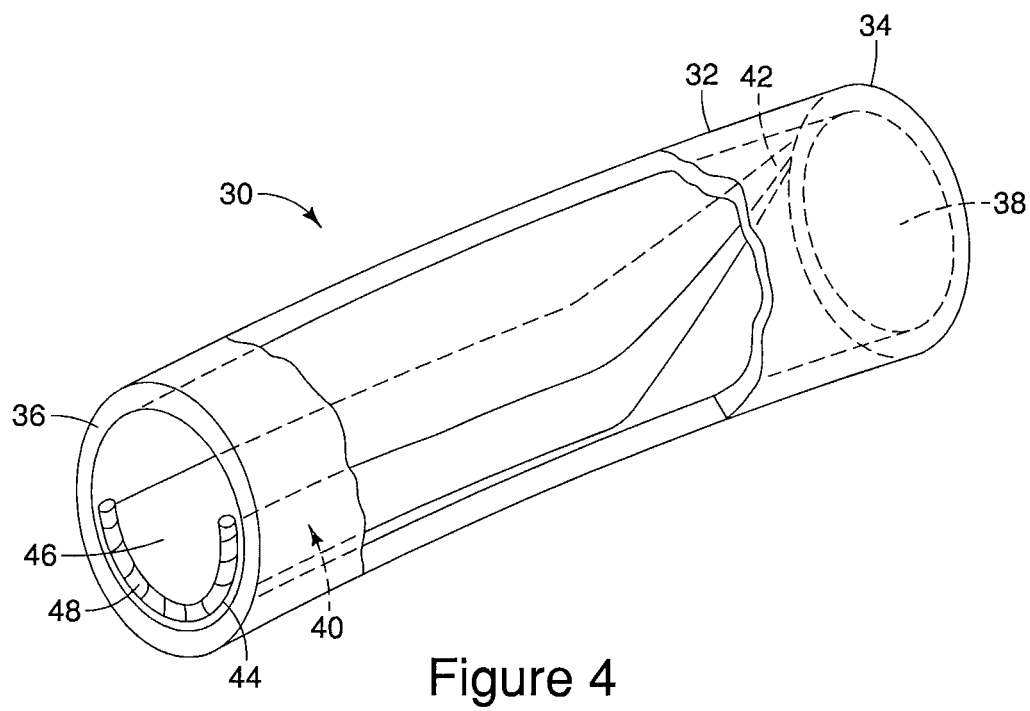
FIG. 4 is a perspective view of FIG. 3 in a closed state.

FIGS. 3 and 4 show a first embodiment of such a perfusion system. FIG. 3 shows a perfusion branch in an open position and FIG. 4 shows the branch in a closed position. As shown in FIG. 3, perfusion branch 30 includes tubular component 32 having proximal 34 and distal ends 36, and lumen 38 extending therebetween. Disposed in lumen 38 is perfusion element 40. Perfusion element 40 may take the form of a valve. Perfusion element 40 has a proximal end 42, a distal end 44, and in this example, a perfusion flap 46. Flap 46 has a sealing member 48 that holds the flap 46 against an inner wall of the tubular component 32 to keep the branch 30 open to fluid flow. Sealing member 48 may be held in place with a biodegradable element 50, such as dissolvable sutures, threads, staples, clips, adhesive and the like, as are known in the art.

In operation, the perfusion branch remains open to allow fluid flow entirely through the perfusion branch to perfuse the aneurysm or branch vessels. After a predetermined period of time, determined by the type of biodegradable element 50 used, the biodegradable element will biodegrade and/or dissolve. At this time, the sealing member 48 is released and is self-biased towards the opposite wall of the branch as shown in FIG. 4, causing the flap 46 to close the lumen 38, thus self-sealing the perfusion branch. In one embodiment the sealing member comprises bi-stable characteristics.

Figure 5:
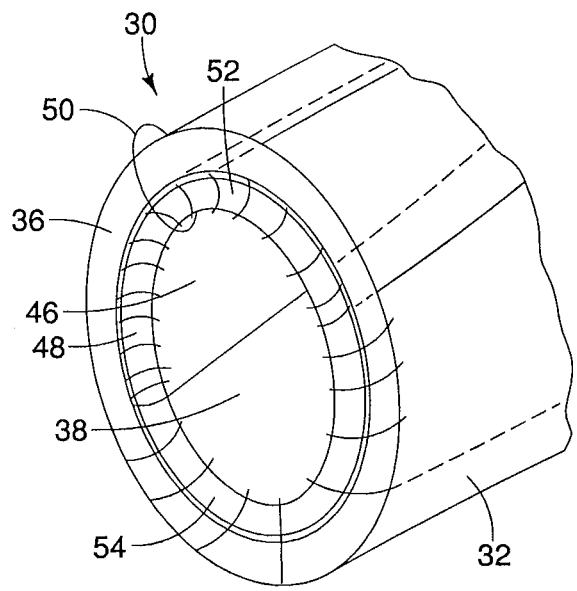
FIG. 5 is a partial perspective view of a second embodiment of a perfusion branch in an open state.
Figure 6:
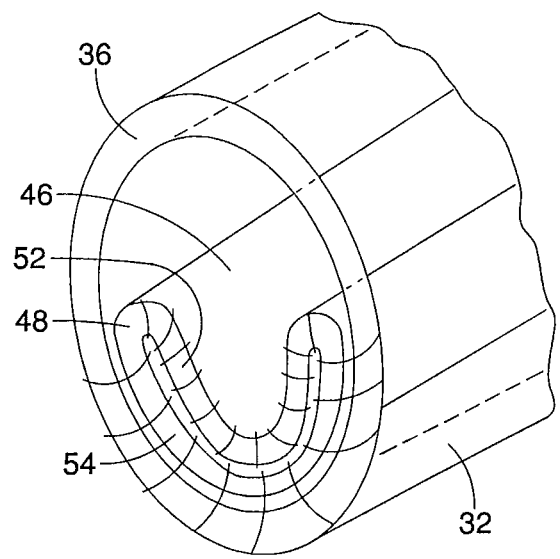
FIG. 6 is a partial perspective view of FIG. 5 in a closed state.

FIGS. 5 and 6 show a second embodiment of such a perfusion system. FIG. 5 shows a perfusion branch in an open position and FIG. 6 shows the branch in a closed position. FIGS. 5 and 6 show a partial perspective view of a distal end of a perfusion branch 30. In this second embodiment, the sealing member 48 is an internal tube. Like the flap 46 of the first embodiment, the tube is held open at at least one end with a sealing member 48, such as a biasing ring. Sealing member 48 is held in its open configuration by one or more biodegradable elements 50 at one portion 52 to maintain its ring shape and hence hold the lumen open as shown in FIG. 5. As shown in FIG. 5, another portion 54 of the sealing member 48 is sutured to the tubular component 32 in a permanent manner with non-biodegradable elements such as sutures, staples, clips, adhesive and the like. After a predetermined period of time, determined by the type of biodegradable element 50 used, the biodegradable element will biodegrade and/or dissolve. At this time, the sealing member 48 is released and is self-biased towards the opposite wall of the branch as shown in FIG. 6, causing the sealing member (the internal tube) to close at at least one end, here shown as the distal end, thus self-sealing the perfusion branch. Alternatively, the sealing element can be at the proximal end of the sealing tube or a sealing element can be at both ends of the tube in this embodiment.

Figure 7:
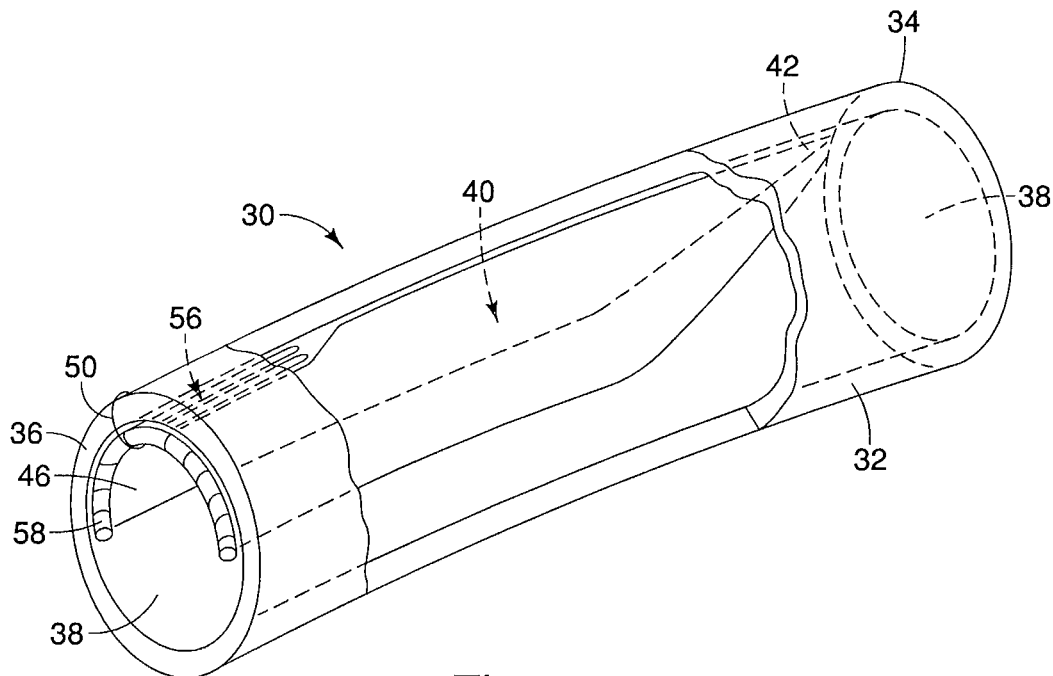
FIG. 7 is a perspective of a third embodiment of a perfusion branch of a stent graft in an open state.
Figure 8:
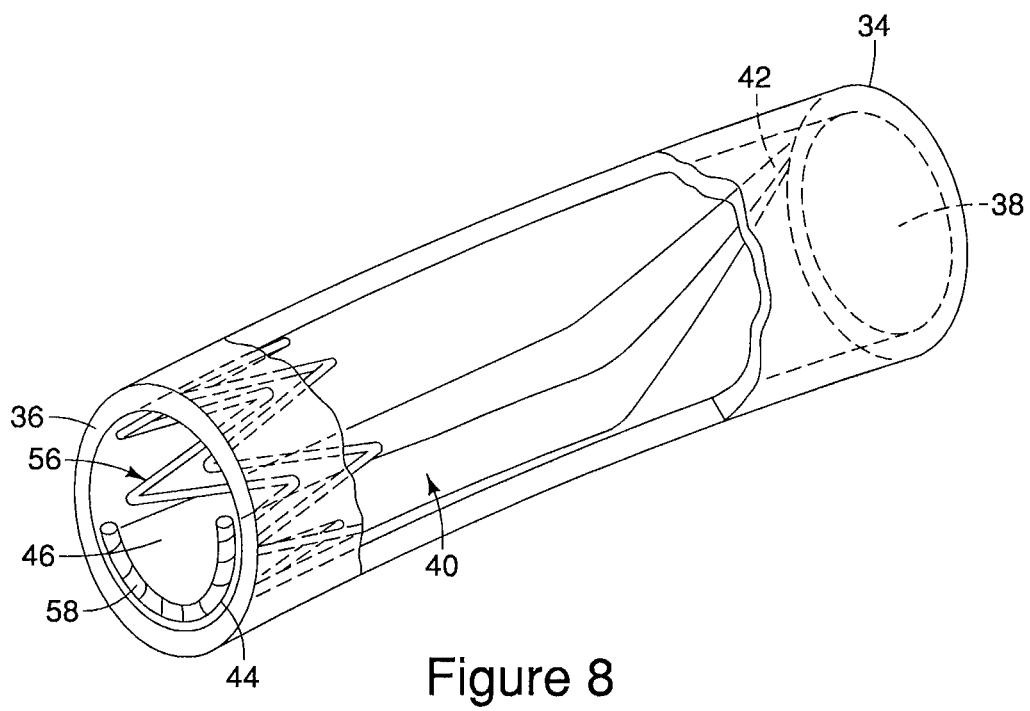
FIG. 8 is a perspective view of FIG. 7 in a closed state.

FIGS. 7 and 8 show a third embodiment of such a perfusion system. FIG. 7 shows a perfusion branch in an open position and FIG. 8 shows the branch in a closed position. FIGS. and 8 are similar to the first embodiment shown in FIGS. 3 and 4, with a distal stent or spring 56 cooperating to bias the flap 46 against the opposite wall of the perfusion branch 30. As shown in FIG. 7, stent 56 is held compressed by the flap 46 which is held against the wall to keep the lumen open by one or more biodegradable elements 50, such as sutures, clips, staples, dissolvable adhesive and the like. In this embodiment, element 58, may not on its own have biasing force. Stent 56 is a self-expanding stent as is known in the art. After a predetermined period of time, determined by the type of biodegradable element 50 used, the biodegradable elements 50 will biodegrade and/or dissolve and the stent 56 will spring open under its self-expanding forces and bias the flap against the opposite wall of the lumen as shown in FIG. 8, thereby sealing the lumen.

Figure 9:
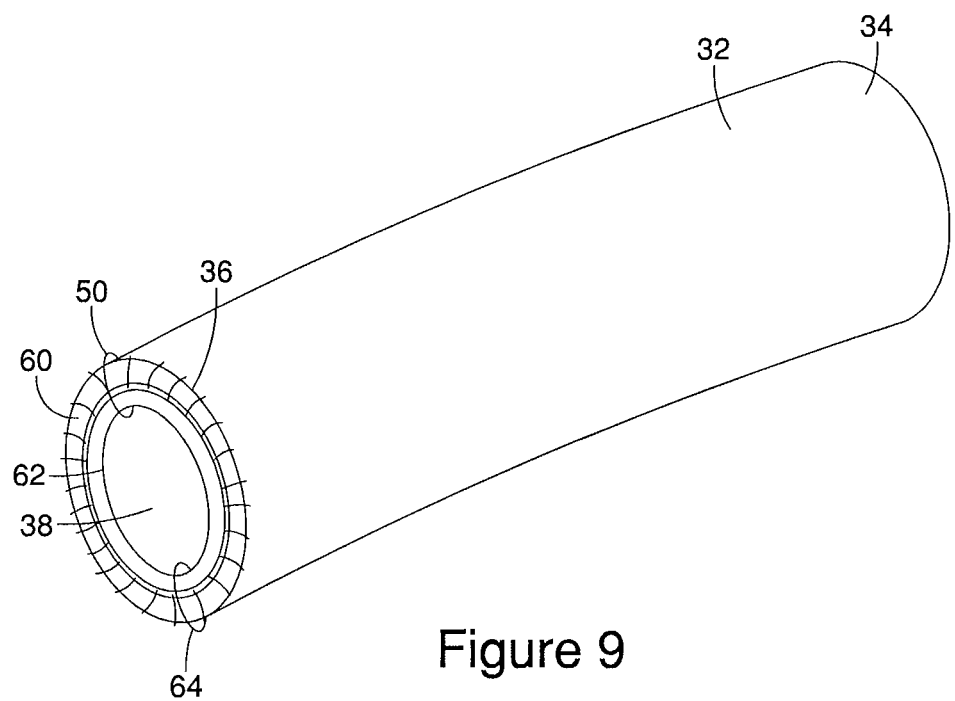
FIG. 9 is a perspective of a fourth embodiment of a perfusion branch of a stent graft in an open state.
Figure 10:
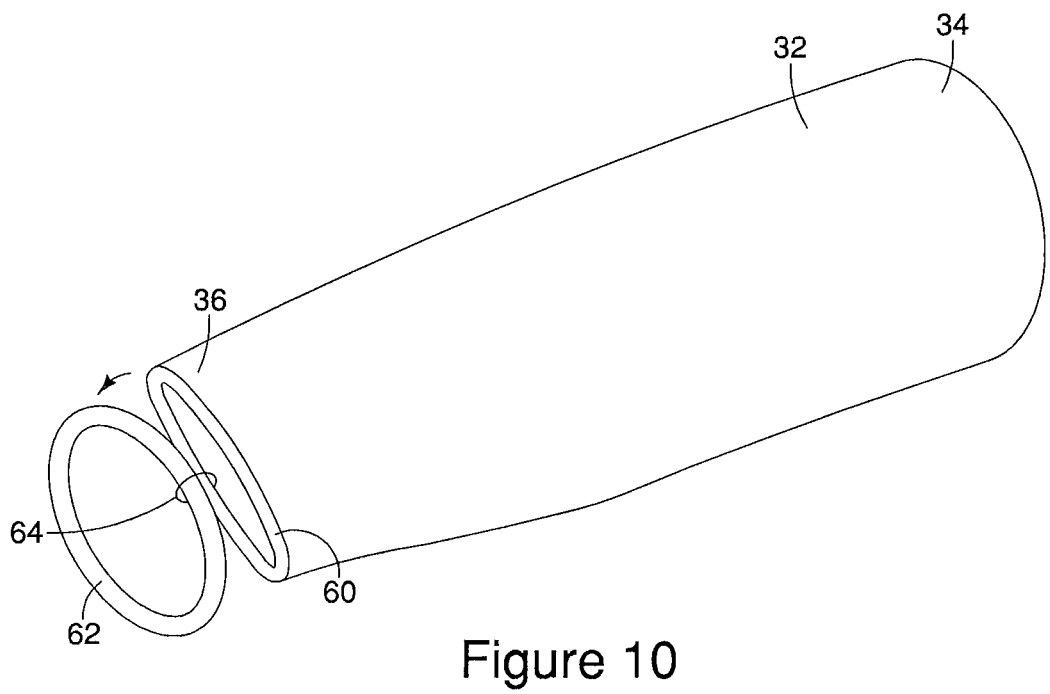
FIG. 10 is a perspective view of FIG. 9 in a closed state.

FIGS. 9 and 10 show a fourth embodiment of such a perfusion system. FIG. 9 shows a perfusion branch in an open position and FIG. 10 shows the branch in a closed position. In FIG. 9, the distal end 36 of the perfusion branch has a double ring structure. The first ring 60 is permanently attached, such as sewing, gluing, enclosing, and the like, to the distal end of the perfusion branch 30 and has a biasing force. The second ring 62 is attached to the first ring 60 by one or more biodegradable elements 50 and maintains ring 60 in a circular shape to keep the lumen open. At least one permanent element, such as a hinge 64 maintains a portion of ring 62 in contact with a portion of ring 60. In this embodiment, the rings are attached to each other. After a predetermined period of time, determined by the type of biodegradable element 50 used, the biodegradable elements 50 will biodegrade and/or dissolve and the second ring 62 will spring away from the distal end. Ring 60, upon being released from the second ring will bias shut. In other words, ring 60 has a relaxed shape that is biased towards the closed position. Rings 60 and 62 may be made of the same material or different materials. For example, ring 60 may be made of shape memory material and ring 62 may be made of another alloy, such as stainless steel. In another embodiment the rings are of the same material but treated such that the ring 60 has its self-closing characteristics.

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. Although specific terms are employed herein, they are used in a generic and descriptive sense only and not for purposes of limitation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment of the invention.

The invention claimed is:

1. A prosthesis comprising:
    a tubular body of a biocompatible graft material having a proximal end, a distal end, a lumen therethrough, and a sidewall; and
    at least one perfusion branch extending from the sidewall of the tubular body having a proximal end, a distal end, and a lumen therethrough, where the lumen of the perfusion branch is in temporary fluid communication with the lumen of the tubular body;
    where the perfusion branch comprises a self-sealing component, that after predetermined period of time precludes fluid flow out of the distal end of the perfusion branch.

2. The prosthesis of claim 1, wherein the self-sealing component comprises a flap element and a biodegradable attachment.

3. The prosthesis of claim 2, wherein the biodegradable attachment comprises one or more dissolvable sutures, staples, clips, adhesive or the like.

4. The prosthesis of claim 2, wherein self-sealing component further includes a biasing element.

5. The prosthesis of claim 4, wherein the biasing element comprises bi-stable properties.

6. The prosthesis of claim 4, wherein the biasing element comprises one or more rings.

7. The prosthesis of claim 6, further comprising a ring that holds the biasing element in an open condition.

8. The prosthesis of claim 7 where the ring is pivotally attached to the biasing element.

9. The prosthesis of claim 1, wherein a first portion of the perfusion branch extends external to the prosthesis and another portion of the perfusion branch is internal to the prosthesis.

10. The prosthesis of claim 1, wherein the self-sealing component comprises a spring.

11. The prosthesis of claim 1, wherein the self-sealing component is a stent.

12. A stent-graft comprising:
    a tubular body of a biocompatible graft material having a proximal end, a distal end, a lumen therethrough, at least one stent attached to the graft material and a sidewall;
    at least one branch extending from the sidewall of the stent graft;
    at least one perfusion branch extending from the sidewall of the tubular body having a proximal end, a distal end, and a lumen therethrough, where the lumen of the perfusion branch is in temporary fluid communication with the lumen of the tubular body;

where the perfusion branch comprises a self-sealing component, that after predetermined period of time precludes fluid flow out of the distal end of the perfusion branch.

13. The prosthesis of claim 12, wherein the self-sealing component comprises a flap element and a biodegradable attachment.

14. The prosthesis of claim 13, wherein the biodegradable attachment comprises one or more dissolvable sutures, staples, clips, adhesive or the like.

15. The prosthesis of claim 13, wherein self-sealing component further includes a biasing element.

16. The prosthesis of claim 15, wherein the biasing element comprises bi-stable properties.

17. The prosthesis of claim 15, wherein the biasing element comprises one or more rings.

18. The prosthesis of claim 17, further comprising a ring that holds the biasing element in an open condition.

19. The prosthesis of claim 12, wherein a first portion of the perfusion branch extends external to the prosthesis and another portion of the perfusion branch is internal to the prosthesis.

20. The prosthesis of claim 12, wherein the self-sealing component comprises a spring.

\* \* \* \* \*